United States Patent [19]

Askanazi et al.

[11] Patent Number: 5,256,669

[45] Date of Patent: Oct. 26, 1993

[54] METHODS AND COMPOSITIONS FOR TREATING ACUTE OR CHRONIC PAIN AND DRUG ADDICTION

[75] Inventors: Jeffrey Askanazi, Haworth, N.J.; David P. Katz, Dobbs Ferry, N.Y.; Tuula Manner, Turku, Finland

[73] Assignee: Aminotek Sciences, Inc., Demarest, N.J.

[21] Appl. No.: 926,719

[22] Filed: Aug. 7, 1992

[51] Int. Cl.$^5$ ............... A61K 31/44; A61K 31/195
[52] U.S. Cl. ............................. 514/282; 514/561
[58] Field of Search ......................... 514/282, 561

[56] References Cited

U.S. PATENT DOCUMENTS 5,006,559  4/1991  Askanazi et al. ............ 514/561
5,017,616  5/1991  Askanazi ...................... 514/561

OTHER PUBLICATIONS

*Goodman and Gilman's The Pharmacological Basis of Therapeutics*, Chapter 21, "Opioid Analgesics and Antagonists", pp. 485–521 (8th ed. 1990).
Ekblom, A. et al., Pain, 44:249–254, "Tryptophan supplementation does not affect postoperative pain intensity or consumption of analgesics" (1991).
Takala et al., Crit. Care Med. 16:465–469, "Changes in respiratory control induced by amino acid infusions" (1988).
Kirvelä, O. et al., Acta Anasesth. Scand. 34:645–648, "Respiratory and sleep patterns during nocturnal infusion of branched chain amino acids" (1990).
Söreide, E. et al., Kidney International 40:539–543, "Branched-chain amino acid in chronic renal failure patients: respiratory and sleep effects" (1991).
Keefe, F. J., *Advances in Pain Measurement*, vol. 12, "Behavioral measurement of pain", pp. 405–424 (C. R. Chapman and J. D. Loeser, eds.) (Raven Press 1989).
G. Woolfe and A. D. MacDonald,"The evaluation of the analgesic action of pethidine hydrochloride Demerol", J. Pharmacol. Exp. Ther. 80:300–307 (1944).
Gil, K. M. et al., Nutrition 6:291–295, "Parenteral nutrition and oral intake: effect of branched chain amino acids" (1990).

*Primary Examiner*—S. J. Friedman
*Attorney, Agent, or Firm*—Elizabeth M. Barnhard

[57] ABSTRACT

Methods and compositions for treating acute or chronic pain in a mammal comprising administering a therapeutically effective amount of an analgesic solution comprising at least one branched chain amino acid selected from the group consisting of leucine, isoleucine, and valine, or administering a therapeutically effective amount of an analgesic solution comprising an analgesic agent selected from the group consisting of an opioid, an agonistic-antagonistic agent, and an anti-inflammatory agent, and at least one branched chain amino acid selected from the group consisting of leucine, isoleucine, and valine. A method and composition for treating addiction to narcotic drugs comprises administering a therapeutically effective amount of a solution comprising methadone and at least one branched chain amino acid selected from the group consisting of leucine, isoleucine, and valine.

11 Claims, 2 Drawing Sheets

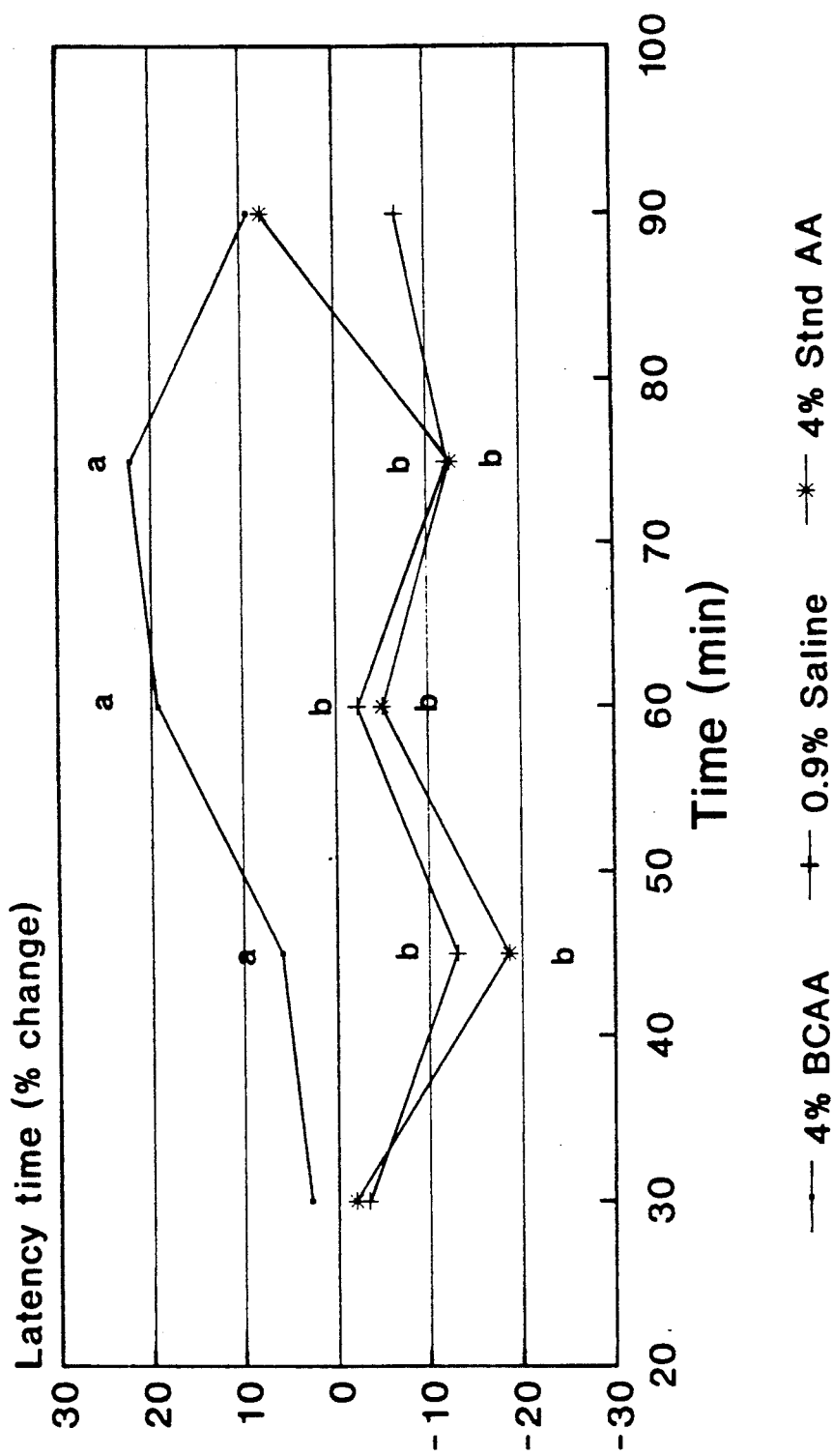

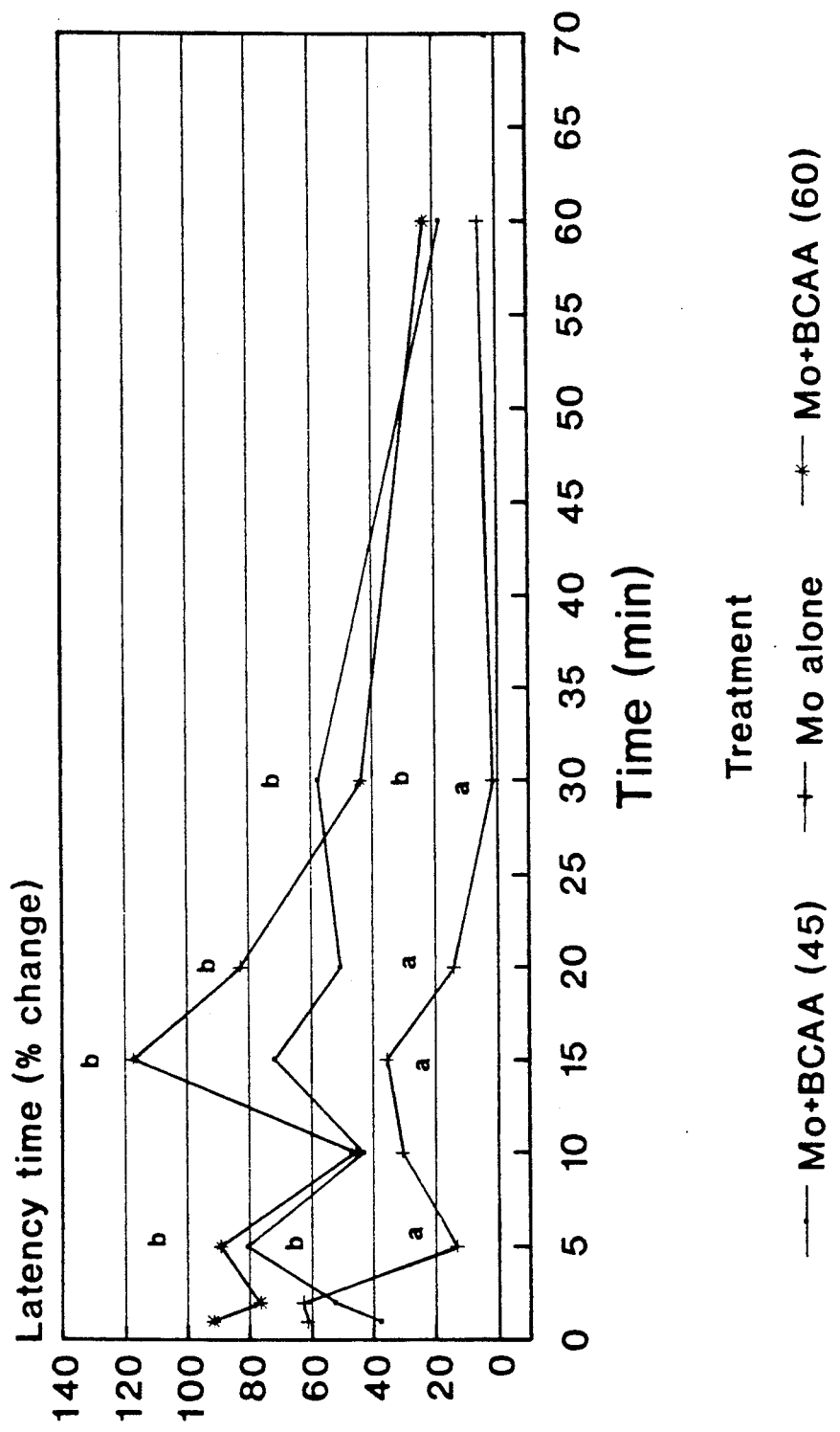

METHODS AND COMPOSITIONS FOR TREATING ACUTE OR CHRONIC PAIN AND DRUG ADDICTION

FIELD OF THE INVENTION

This invention relates to methods and compositions for treating acute or chronic pain in a mammal comprising administering a therapeutically effective amount of an analgesic solution comprising at least one branched chain amino acid selected from the group consisting of leucine, isoleucine, and valine or by administering a therapeutically effective amount of an analgesic solution comprising an analgesic agent selected from the group consisting of an opioid, an agonistic-antagonistic agent, and an anti-inflammatory agent, and at least one branched chain amino acid selected from the group consisting of leucine, isoleucine, and valine; and to a method and composition for treating drug withdrawal from narcotic drugs comprising administering a therapeutically effective amount of a solution comprising methadone and at least one branched chain amino acid selected from the group consisting of leucine, isoleucine, and valine.

BACKGROUND OF THE INVENTION

The pain response is a protective reflex system warning an individual of hostile situations and tissue injury. The origins of clinically significant acute and chronic pain in a mammal are different, but the biochemical and neurological pathways are similar. In the following discussion on pain and its management, the focus is primarily on humans, however, it should be understood that the concepts of pain are applicable to mammalian animals and the management of such pain is applicable to veterinary medicine.

Acute pain is often associated with surgery and with trauma. The intensity of acute postoperative pain varies considerably depending on the extent of the surgical procedure performed, on the individual's pain sensitivity, and on the type of anesthetic management employed during surgery. In general, major operations on the thorax and the upper abdominal region induce the most intensive postoperative pain. Extensive orthopedic operations also produce strong postoperative pain.

Chronic pain can be somatogenic, neurogenic, or psychogenic in origin. Somatogenic pain can be muscular or skeletal (i.e., osteoarthritis, lumbosacral back pain, posttraumatic, myofascial) visceral (i.e., chronic pancreatitis, ulcer, irritable bowel), ischemic (i.e., arteriosclerosis obliterans), or related to the progression of cancer. Neurogenic pain can be due to posttraumatic and postoperative neuralgia, can be related to neuropathies (i.e., diabetes, toxicity, etc.), and can be related to nerve entrapment, facial neuralgia, perineal neuralgia, postamputation, thalamic, causalgia, and reflex sympathetic dystrophy.

The modern concept of pain treatment emphasizes the significance of prophylactic prevention of pain, as pain is more easily prevented than relieved. Additionally, the hormonal stress responses associated with pain are considered harmful to the patient, impair the healing process and overall recovery, and generally are to be avoided. Pain is generally controlled by the administration of analgesic agents Analgesic agents include opiates, agonistic-antagonistic agents, and anti-inflammatory agents.

Opiates, a class of centrally acting compounds, are the most frequently used agents for pain control. Opiates are narcotic agonistic analgesics and are drugs derived from opium, such as morphine, codeine, and many synthetic congeners of morphine, with morphine being the most widely used derivative. Opioids are natural and synthetic drugs with morphine-like actions and include the opiates. Opioids are narcotic agonistic analgesics which produce drug dependence of the morphine type and are subject to control under federal narcotics law because of their addicting properties. The term "opioids" also includes opioid antagonists that are essentially devoid of agonist activity at any opioid receptor, partial agonists, and opioids with mixed actions, i.e., agonist-antagonists, which are agonists at some receptors and antagonists at other receptors.

The chemical classes of opioids with morphine-like activity are the purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives. The principal phenanthrenes are morphine, codeine, and thebaine. The principal benzoisoquinolines are papaverine, a smooth muscle relaxant, and noscapine. Semi-synthetic derivatives of morphine include diacetylmorphine (heroin), hydromorphone, oxymorphone, hydrocodone, apomorphine, etorpine, and oxycodone. Phenylpiperidine derivatives include meperidine and its congeners diphenoxylate and loperamide, alphaprodine, anileridine hydrochloride or phosphate, and piminodine esylate. Morphinan derivatives include levorphanol. The diphenyl-heptane derivatives include methadone and its congeners, and propoxyphene. Propionanilide derivatives include fentanyl citrate and its congeners sufenil citrate and alfenatil hydrochloride. These opioid analgesics are discussed in detail in *Goodman and Gilman's The Pharmacological Basis of Therapeutics*, Chapter 21, "Opioid Analgesics and Antagonists", pp. 485–521 ($8^{th}$ ed. 1990), which is incorporated herein by reference.

The most commonly used pain treatment during the immediate postoperative period is the repeated administration of opioids, whether intravenously, intramuscularly, or subcutaneously. The potency of all opioids is roughly comparable and can be effective against the most severe pain with appropriate dosing at intervals. However, all of these opioids have a wide variety of side effects which can minimize their effectiveness in certain situations.

The side effects associated with the use of opioids include respiratory depression, reduced cough reflex, bronchial spasms, nausea, vomiting, release of histamine, peripheral vasodilation, orthostatic hypotension, vagal impact on the heart, contraction of smooth muscles (sphincters), reduced peristaltic motility in the gastrointestinal tract, urinary retention, stimulated release of adrenalin, anti-diuretic hormone, changes in the regulation of body temperature and sleep pattern, tolerance and addiction.

The negative effects on respiratory function are of special importance to the postoperative mammalian patient. During the course of major surgery under general anesthesia, a mammalian patient is typically put to sleep with anesthetic agents, is paralyzed with muscle relaxants, is intubated and placed on mechanical ventilation, and is given analgesic agents. All of these treatments have direct and indirect effects on depressing respiratory drive with the net consequence that postoperatively the mammalian patient may have trouble breathing. As opiates may cause respiratory depression, reduce the cough reflex, and cause bronchial spasms, it is not advisable to administer opiates to mammalian patients for pain control immediately after surgery in order to avoid impairing respiratory function. Conversely, the mammalian patient is deprived of effective postoperative pain control because the administration of opiates is contraindicated due to the impact on respiratory function.

In addition to the opioids, other classes of analgesic agents that are commonly used include agonistic-antagonistic analgesic agents, non-steroidal anti-inflammatory drugs, and psychoactive drugs. Agonistic-antagonistic analgesic agents are effective against moderate to severe pain, but due to their antagonistic properties, their analgesic efficacy does not increase by increasing the dosage above a certain level. Furthermore, higher doses of agonistic-antagonistic analgesic agents are often associated with unpleasant sympathomimetic and psychomimetic side effects such as tachycardia, increase in blood pressure, and agitation. However, the risk of respiratory depression also decreases in line with the diminished analgesic activity of the higher doses. Agonistic-antagonistic analgesic agents with pharmacological activity similar to morphine-like opioids include pentazocine, nalbuphine, butorphanol, nalorphine, buprenorphine (a partial agonist), meptazinol, dezocine, and cyclazocine.

The non-steroidal anti-inflammatory drugs include the salicylates such as salicylamide and acetylsalicylic acid (aspirin); the para-aminophenol derivatives such as acetaminophen and phenacetin; the pyrazole derivatives such as antipyrine, aminopyrine, and dypyrone; and nefenamic acid, indomethacin, methimazole, paracetamol, diclophenac sodium, ibuprofen, naproxene, and ketorolac tromethamine, which can be combined with opioids or used alone to alleviate milder pain after superficial surgical procedures. The mechanism of action of non-steroidal anti-inflammatory drugs is on the site of tissue injury to peripherally inhibit cyclooxygenase, the enzyme responsible for providing an activated substrate for the synthesis of prostaglandins which are a group of short-acting mediators of inflammation. The maximal analgesic effect of non-steroidal anti-inflammatory drugs is comparable to five milligrams of morphine administered intramuscularly, and when given in combination with opioids, the analgesic efficacy is additive. Side effects of non-steroidal anti-inflammatory agents include gastrointestinal irritation, bronchospastic effects in asthmatic mammalian patients, and tinnitus.

These different classes of analgesic agents are similarly used to treat chronic pain in mammals. However, mammals often experience tolerance and develop a physical dependency on these analgesic agents, especially the opioids, thereby reducing the effectiveness of the pain treatment and continuing the suffering from the chronic pain.

Physical dependence or drug addiction to narcotic drugs, i.e., opioids, has been traditionally treated by drug withdrawal through withholding the opioid from the drug dependent individual, gradually decreasing the amount of opioid taken by the individual over time, administering an opioid antagonistic drug, or substituting another drug, such as methadone, buprenorphine, or methadyl acetate, for the opioid to ameliorate the physical need for the opioid. When an opioid is discontinued, withdrawal symptoms appear, the character and severity of which are dependent upon such factors as the particular opioid being withdrawn, the daily dose of the opioid that is being withdrawn, the duration of use of the opioid, and the health of the drug dependent individual. The pain associated with withdrawal symptoms can be quite severe.

For example, the withdrawal of morphine, heroin, or other opioid agonists with similar durations of action from an individual dependent upon the opioid gives rise to lacrimation, rhinorrhea, yawning, and sweating 8 to 12 hours after the last dose of the opioid. As withdrawal progresses, the individual will be subject to dilated pupils, anorexia, gooseflesh, restlessness, irritability, and tremor. At the peak intensity of withdrawal, which is 48 to 72 hours for morphine and heroin, the individual suffers from increasing irritability, insomnia, marked anorexia, violent yawning, severe sneezing, lacrimation, coryza, weakness, depression, increased blood pressure and heart rate, nausea, vomiting, intestinal spasm, and diarrhea. The individual commonly experiences chills alternating with hot flushes and sweating, as well as abdominal cramps, muscle spasms and kicking movements, and pains in the bones and muscles of the back and extremities, and exhibits leukocytosis and an exaggerated respiratory response to carbon dioxide. Typically the individual does not eat or drink which, when combined with the vomiting, sweating, and diarrhea, results in weight loss, dehydration, and ketosis. The withdrawal symptoms from morphine and heroin usually disappear in 7 to 10 days, but the drug dependent individual suffers greatly during the withdrawal period. If an opioid antagonistic drug is administered to the individual, such as naloxone, withdrawal symptoms develop within a few minutes after parenteral administration and reach peak intensity within 30 minutes, with a more severe withdrawal than from withholding the opioid. Withdrawal of morphine-like opioids will produce the same or similar withdrawal symptoms, with the intensity of the symptoms dependent upon the duration of action of the morphine-like opioid.

The drug withdrawal symptoms and the pain associated with them will be alleviated if a suitable opioid is given to the individual, however, this could result in the individual merely substituting dependency on one opioid for another. In the case of individuals dependent upon opioids such as morphine or heroin, methadone, an opioid with morphine-like activity, is given to the drug dependent individual on a daily basis. The methadone suppresses the opioid withdrawal symptoms and diminishes the euphoric effects of all opioids, but if the methadone is abruptly withdrawn, withdrawal symptoms similar to those from morphine will appear, albeit of less intensity but more prolonged.

An alternative approach to pain treatment employing the analgesic agents described above was tried in which an aromatic amino acid, tryptophan, was administered to persons undergoing third molar surgery to alleviate the pain and reduce or eliminate the consumption of other analgesics. The rationale was that serotonin, a neurotransmitter and a component of the serotonergic pain suppressing pathway, is synthesized from tryptophan after the tryptophan is transported across the blood-brain-barrier, it having been believed that tryptophan as a precursor for serotonin would have pain alleviating effects. It was found, however, that tryptophan had no effect on postoperative pain or on the consumption of other analgesics. Ekblom, A., et al., Pain, 44:249–254, "Tryptophan supplementation does not affect postoperative pain intensity or consumption of analgesics" (1991).

Accordingly, an object of the invention is to provide methods and compositions for the treatment of acute or chronic pain which provide effective control of pain without the harmful side effects associated with traditional analgesics, such as respiratory depression, disturbed sleep patterns, decrease in appetite, and physical dependency. Another object of the invention is to provide a method and a composition for the treatment of addiction to narcotic drugs which provides for withdrawal from the narcotic drug without withdrawal symptoms and without the pain associated with withdrawal symptoms. A further object of the invention is to provide a method for the treatment of addiction to a narcotic drug which eliminates the dependency on the replacement drug, methadone, for the narcotic drug. These and other objects and features of the invention will be apparent from the following description.

BRIEF DESCRIPTION OF THE DRAWINGS

FIG. 1 is a graph comparing the effect of branched chain amino acids, saline, and a standard amino acid solution on the latency time of the pain response in rats subjected to a hot plate analgesia test. The graph illustrates the mean percent change in latency time from baseline measurement over the time course of the experiment.

FIG. 2 is a graph similar to FIG. 1 in which the same hot plate analgesia test of FIG. 1 was employed to compare the effects on the percent change in latency time from baseline measurements of the pain response in rats of morphine alone; morphine and branched chain amino acids administered 45 minutes prior to morphine administration; and morphine and branched chain amino acids administered 60 minutes prior to the administration of morphine.

SUMMARY OF THE INVENTION

The present invention provides a method of treating acute or chronic pain in a mammal by the administration of a therapeutically effective amount of an analgesic solution comprising at least one branched chain amino acid selected from the group consisting of leucine, isoleucine, and valine. It has surprisingly been found that these branched chain amino acids have an analgesic effect.

An advantage of this method is that the branched chain amino acid analgesic solution provides effective control of pain without the harmful side effects associated with traditional analgesics.

The present invention also provides a method of treating acute or chronic pain in a mammal by the administration of a therapeutically effective amount of an analgesic solution comprising an analgesic agent selected from the group consisting of an opioid, an agonistic-antagonistic agent, and an anti-inflammatory agent, and at least one branched chain amino acid selected from the group consisting of leucine, isoleucine, and valine.

The present invention also provides an analgesic solution comprising an analgesic agent selected from the group consisting of an opioid, an agonistic-antagonistic agent, and an anti-inflammatory agent, and at least one branched chain amino acid selected from the group consisting of leucine, isoleucine, and valine.

An advantage of this analgesic solution is that it provides effective control of pain without the harmful side effects associated with traditional analgesics.

The present invention also provides a method for treating addiction to narcotic drugs by administration of a therapeutically effective amount of a solution comprising methadone and at least one branched chain amino acid selected from the group consisting of leucine, isoleucine, and valine.

An advantage of this method is that it provides an effective, pain-controlling method of drug withdrawal.

A further advantage is that the methadone in the solution may be replaced over time by the non-addictive branched chain amino acids. Dependency on methadone may be eliminated without the withdrawal symptoms associated with the withdrawal of methadone.

Upon further study of the specification and appended claims, further objects and advantages of this invention will become apparent to those skilled in the art.

DETAILED DESCRIPTION OF THE INVENTION

It is to be understood that while the present invention is primarily contemplated for humans, it is also contemplated for use in veterinary medicine.

In the present invention, a mammal having acute or chronic pain may be treated by administering to the mammal a therapeutically effective amount of an analgesic solution comprising at least one branched amino acid selected from the group consisting of leucine, isoleucine, and valine in an amount of about 1 to 100%, preferably 4%, by weight of the analgesic solution, and purified water. If the analgesic solution is to be administered parenterally, the analgesic solution is made with sterile water. Surprisingly, branched chain amino acids have an analgesic effect, as demonstrated in Example I below.

Preferably, the branched chain amino acids of the analgesic solution are leucine, isoleucine, and valine and are present in a ratio by weight of about 0.1–10:0.1–10:0.1:10, preferably about 1:1:1. The preferred analgesic solution is prepared by mixing 1:38 g leucine, 1.38 g isoleucine, and 1.24 g valine in 100 ml purified or sterile water to produce a solution containing 4% by weight of branched amino acids in a ratio of about 1:1:1.

The mammal may also be treated by administering an analgesic solution comprising at least one branched chain amino acid selected from the group consisting of leucine, isoleucine, and valine in an amount of at least 1% by weight of the analgesic solution, and an analgesic agent selected from the group consisting of an opioid, an agonistic-antagonistic agent, and an anti-inflammatory agent. The dosage amount of the analgesic agent is dependent on the mode of administration (parenteral, enteral, subcutaneous, or intramuscular), the weight of the mammal, and the particular analgesic agent being used. One skilled in the art will be able to adjust the dosage amount accordingly for the mammal being treated.

When the analgesic agent is an opioid, the dosage amount is about from 0.2 to 30 mg per kg of body weight per day. The opioid may be a phenanthrene, a benzylisoquinoline, a semi-synthetic derivative of morphine, a phenylpiperidine derivative, a morphinan derivative, a benzomorphan derivative, a diphenylheptane derivative, or a propionanilide derivative. If the solution is to be parenterally administered to the mammal, then the dosage amount of the opioid is about 0.2 to 10 mg per kg of body weight per day.

The opioid may be instead administered separately after administration of an analgesic solution containing at least one branched chain amino acid. If the opioid is administered separately, the opioid should be administered at a time to achieve the maximum synergistic analgesic effect of the branched chain amino acid(s) and the opioid. Example II demonstrates that in the rat it is preferable to administer the opioid 45 to 60 minutes after administration of the analgesic solution containing at least one branched chain amino acid to achieve the maximal combined analgesic effect of the branched chain amino acid solution and the opioid. The timing may vary somewhat from species to species of mammal, but the timing will be readily ascertainable by one skilled in the art.

When the analgesic agent is an agonistic-antagonistic agent, the dosage amount is about from 0.2 to 90 mg per kg of body weight per day. The agonistic-antagonistic agent may be pentazocine, nalbuphine, butorphanol, nalorphine, buprenorphine, meptazinol, dezocine, and cyclazocine. If the analgesic solution is to be administered parenterally, then the dosage amount of the agonistic-antagonistic agent is about 0.2 to 10 mg per kg of body weight per day. Like the opioid, the agonistic-antagonistic agent may be administered separately after administering an analgesic solution containing at least one branched chain amino acid.

When the analgesic agent is an anti-inflammatory agent, the dosage amount is about from 1.0 to 60 mg per kg of body weight per day. The anti-inflammatory agent may be a salicylate, a para-aminophenol derivative, a pyrazole derivative, nefenamic acid, indomethacin, methimazole, paracetamol, diclophenac sodium, ibuprofen, naproxene, and ketorolac tromethamine. If the analgesic solution is to be administered parenterally, then the dosage amount of the anti-inflammatory agent is about 1.0 to 10 mg per kg of body weight per day. Like the opioid, the anti-inflammatory agent may be administered separately after administering an analgesic solution containing at least one branched chain amino acid.

It is expected that a lesser dosage amount of the analgesic agent will be needed due to the potentiating effect of branched chain amino acids on the analgesic agent (see Example II below), as well as the analgesic effect of the branched chain amino acids.

The analgesic solution of the present invention comprises a therapeutically effective amount of an analgesic agent selected from the group consisting of an opioid, an agonistic-antagonistic agent, and an anti-inflammatory agent, and at least one branched chain amino acid selected from the group consisting of leucine, isoleucine, and valine in an amount of at least 1% by weight of the analgesic solution. The opioid, the agonistic-antagonistic agent, and the anti-inflammatory agent may be selected from the alternatives described above in the discussion of the methods of treatment of acute or chronic pain. The dosage amounts of the analgesic agent is the same as described above in the methods of treatment of acute or chronic pain and is dependent on the mode of administration (parenteral, enteral, subcutaneous, or intramuscular), the weight of the mammal, and the particular analgesic agent being used.

A benefit of an analgesic solution containing branched chain amino acids and an opioid as the analgesic agent is that the branched chain amino acids increase the sensitivity of the ventilatory drive, normalize disturbed sleep patterns, and enhance or stimulate mood and appetite, which effects are the direct opposite of the adverse side effects of opioids. See U.S. Pat. No. 5,006,559; U.S. Pat. No. 5,017,616; Takala et al., Crit. Care Med. 16:465-469, "Changes in respiratory control induced by amino acid infusions" (1988); Gil, K. M. et al., Nutrition 6:291-295, "Parenteral nutrition and oral intake: effect of branched chain amino acids" (1990); Kirvelä, O. et al., Acta Anaesth. Scand. 34:645-648, "Respiratory and sleep patterns during nocturnal infusion of branched chain amino acids" (1990); Söreide, E. et al., Kidney International 40:539-543, "Branched-chain amino acid in chronic renal failure patients: respiratory and sleep effects" (1991). It can therefore be expected that a mammal treated with this analgesic solution will have the pain suppressed and will feel better than if treated with an opioid only.

In addition to the analgesic solution of the present invention, the present invention also provides a solution for use in the treatment of a mammal's drug addiction to narcotic drugs comprising a therapeutically effective amount of methadone, at least one branched chain amino acid selected from the group consisting of leucine, isoleucine, and valine, and purified water. The branched chain amino acid(s) is present in an amount of from about 1 to 100% by weight of the solution. The dosage amount of the methadone is preferably from about 10 to 80 mg per kg of body weight.

Preferably, the branched chain amino acids of the solution are leucine, isoleucine, and valine in a ratio by weight of from about 0.1-10:0.1-10:0.1-10. The preferred ratio is about 1:1:1.

An individual who should withdraw from a narcotic drug or is undergoing withdrawal from a narcotic drug may be treated by administering to the individual a therapeutically effective amount of the aforesaid solution. Administration of this solution enables the individual to withdraw from the narcotic drug and eliminate dependency on the narcotic drug without the drug withdrawal symptoms and the pain associated with those symptoms.

As the branched chain amino acids potentiate the effect of methadone, less methadone will be required thereby reducing the dependency on methadone which typically occurs in the treatment of drug addiction to a narcotic drug such as morphine or heroin. Long term dependency on methadone as a replacement for a narcotic drug is not desirable as this merely substitutes one drug dependency for another. Dependency on methadone can be safely and painlessly eliminated by gradually replacing the methadone in increasing amounts with the branched chain amino acids until the individual is receiving a solution containing 100% branched chain amino acids and no methadone. The benefit of this stepwise method of treatment is that dependency on the narcotic drug and the subsequent dependency on the replacement drug, methadone, is eliminated without the pain and other symptoms associated with withdrawal from these drugs.

The following examples illustrate the effects of the present invention.

EXAMPLES

To measure the effect of an analgesic solution containing branched chain amino acids on the pain response, the hot plate analgesia test in which pain response is measured as a function of latency time was employed based on the test protocol described in Keefe, F. J., *Advances in Pain Measurement*, Vol. 12, "Behavioral measurement of pain", pp. 405-424 (C. R. Chapman and J. D. Loeser, eds.)(Raven Press 1989). The hot plate test was first described in 1944 by G. Woolfe and A. D. MacDonald in an article entitled "The evaluation of the analgesic action of pethidine hydrochloride Demerol" in J. Pharmacol. Exp. Ther. 80:300-307.

The animals used in the tests described in the following examples were male Sprague Dawley rats weighing 300 to 350 grams. In the hot plate test employed in the examples, a hot plate analgesia meter (Model 39-D, Innovators in Instrumentation Inc., Cal.) was used to measure hot-plate latency, i.e., the time to exhibit a response to the heat, as a measure of pain response. The hot plate analgesia meter consists of a thermoconducting surface with built-in highly sensitive thermoswitches encased in a box with an automatic timing device. The hot plate was heated to 55° C.±0.2° C. and the animal was placed on the center. The latency time of the animal to show a nociceptive (pain) response from when it was first placed on the hot plate analgesia meter was recorded. The nociceptive (pain) response of the animal was identified by (1) licking of a hind paw, (2) rapid movement (jumping) of the rear paws, or (3) jumping out the enclosure. The animal was removed immediately after demonstrating a pain response. However, to prevent thermal injury, a cut-off point of 20 seconds was set during the testing period.

Before administration of any material to be tested, each animal was pre-tested on the hot plate two times with at least a ten minute interval between tests and the response time results were averaged to give a baseline measurement. The material to be tested was injected intravenously into a tail vein and the latency time of the pain response was measured on the hot plate analgesia meter as described above. The test data is expressed as the percent change in the animal's response to the test material as compared to the animal's baseline measurement.

EXAMPLE I

Comparative Test of Branched Chain Amino Acid Solution v. Saline v. Standard Amino Acid Solution Three experimental groups with a minimum of 8 rats per time point per group were tested for pain response using the hot plate analgesia test described above. After the pre-testing, the rats were injected intravenously in a blind, randomized fashion with one of the following:
1. Physiological 0.9% normal saline as a control ("0.9% Saline").
2. 4% standard amino acid solution ("4% Stnd AA") made by diluting 8.5% Travosol (Baxter Laboratories; Deerfield, Ill.) with sterile water. The animal received a dose containing 320 mg amino acids/kg in a volume of 8 ml/kg.
3. 4% branched chain amino acid solution ("4% BCAA") containing leucine, isoleucine, and valine in a ratio of 1:1:1 (Branchamin 4% Baxter Laboratories, Deerfield, Ill.). The animal received a dose containing 320 mg branched chain amino acids/kg in a volume of 8 ml/kg.

After injection, rats were tested on the hot plate analgesia meter in accordance with the procedure described above. Groups of animals were tested at the time point intervals of 30, 45, 60, 75, and 90 minutes after injection. Animals were tested only at two additional time points after treatment.

The mean percent change in latency time for each experimental group at each time point interval was calculated and plotted on the graph in FIG. 1. Means with different letters at each time point (a and b) are significantly different by analysis of variance with post-hoc comparisons by Tukey test at $p<0.01$. As shown in FIG. 1, the animals that received the 4% BCAA solution had a significantly greater percent change in latency time at 45, 60, and 75 minutes as compared to the 0.9% Saline control and 4% Stnd AA solution. The increase in the percent change of latency time indicates that the 4% BCAA solution ameliorated the rats' pain response elicited by the hot plate analgesia test and therefore had significant analgesic properties.

EXAMPLE II

Comparative Test of Morphine/Branched Chain Amino Acid Solution v. Morphine Solution Three experimental groups with a minimum of five rats per time point per group were studied to assess whether there was an interaction between the analgesic effects of branched chain amino acids and morphine, as a representative opioid analgesic agent. The change in latency time from baseline was measured as a measure of the pain response using the hot plate analgesia test described above. All the animals were pre-tested to obtain baseline measurements.

The rats were subsequently injected intravenously according to one of the three following protocols in order to obtain the peak analgesic effects of branched chain amino acids:
1. Group I rats ("Mo alone") were the control group and were injected with physiological 0.9% normal saline. The volume that the animal received was 8 ml/kg of body weight, as a control. Forty-five minutes after the injection of 0.9% saline, each rat was injected intravenously with 3 mg/kg of body weight of morphine.
2. Group II rats ("Mo+BCAA (45)") were injected intravenously with 8 ml/kg of body weight of the 4% BCAA solution of Example I. Forty-five minutes after injection of the 4% BCAA solution, each rat was intravenously injected with 3 mg/kg of body weight morphine.
3. Group III rats ("Mo+BCAA (60)") were injected intravenously with 8 ml/kg of body weight of the 4% BCAA solution of Example I. Sixty minutes after injection of the 4% BCAA solution, each rat was intravenously injected with 3 mg/kg of body weight of morphine.

After the injection of morphine, groups of rats were tested for latency time of the pain response on the hot plate analgesia meter, in accordance with the procedure described above, at the time point intervals of 1, 2, 5, 10, 15, 20, 30, and 60 minutes after injection. Animals were tested only at two additional time points after treatment.

The mean percent change in latency time for each experimental group at each time point interval was calculated and plotted on the graph in FIG. 2. Means with different letters at each time point (a and b) are significantly different by analysis of variance with post-hoc comparisons by Tukey test at $p<0.01$. As shown in FIG. 2, the morphine and saline control ("Mo alone") had a peak analgesic effect, as measured by the percent change in latency time, at one to two minutes and rapidly dropped off to baseline thereafter. In contrast, both groups of rats preinjected with branched chain amino acids and then morphine ("Mo+BCAA (45)" and "Mo+BCAA (60)") had significantly greater percent changes in latency times at 5,15, 20, and 30 minutes after the injection of morphine when compared to the control group which received morphine and saline. The combination of branched chain amino acids and morphine also produced a greater percent change in latency time at 30 and 45 minutes compared to the 4% BCAA solution alone, which had analgesic properties (see FIGS. 1 and 2). Additionally, both Group II and Group III rats displayed more prolonged analgesic tendencies when compared to the control group receiving morphine and saline. These test results demonstrate that a synergistic analgesic effect is obtained in an animal receiving both branched chain amino acids and morphine, whether they are injected 45 minutes or 60 minutes apart. These results also demonstrate that branched chain amino acids potentiate and prolong the analgesic effect of morphine.

The foregoing examples teach that a solution of branched chain amino acids alone has an analgesic effect. When a solution of branched amino acids is administered with an opioid analgesic such as morphine, the branched chain amino acids potentiate the analgesic effect of the opioid analgesic to produce a synergistic analgesic effect in the mammal. This synergistic effect permits a reduction in the amount of the opioid analgesic used to achieve the same level of pain treatment thereby reducing or even eliminating the risk of the detrimental side effects of opioid analgesics. Even if a larger amount of the opioid analgesic is used, the effects of branched chain amino acids of increasing the sensitivity of the ventilatory drive, normalizing disturbed sleep patterns, and enhancing or stimulating mood and appetite, will offset the adverse side effects of the opioid analgesic, to the benefit of the mammal.

The above description is meant to be illustrative only of the present invention, and not limiting thereof. Other variations of method, composition, and manufacture are well known to those skilled in the art and are meant to be included herein.

We claim:

1. A method for treating acute or chronic pain in a mammal comprising administering to the mammal a therapeutically effective amount of an analgesic solution comprising at least one branched chain amino acid selected from the group consisting of leucine, isoleucine, and valine, wherein the branched chain amino acid is present in an amount of about 1 to 100% by weight of the analgesic solution and an opioid in a dosage amount of about from 0.2 to 30 mg/kg of body weight/day.

2. The method of claim 1, wherein the solution is parenterally administered to the mammal and the dosage amount of the opioid is about 0.2 to 10 mg/kg of body weight/day.

3. The method of claim 1, further comprising separately administering an opioid to the mammal after administering the analgesic solution.

4. An analgesic solution comprising:
   a) a therapeutically effective amount of an analgesic agent consisting of an opioid; and
   b) at least one branched chain amino acid selected from the group consisting of leucine, isoleucine, and valine in an amount of at least 1% by weight of the analgesic solution.

5. The solution of claim 4, wherein the analgesic agent is an opioid and is present in a dosage amount of from about 0.20 to 30 mg/kg of body weight/day.

6. The solution of claim 5, wherein the opioid is morphine.

7. The solution of claim 5, wherein the solution is a parenteral solution and the opioid is present in an amount of from about 0.2 to 10 mg/kg of body weight/day.

8. The solution of claim 4, wherein the branched chain amino acids are leucine, isoleucine, and valine and are present in a ratio by weight of about 0.1–10:0.1–10:0.1–10.

9. A solution for use in treating addiction to narcotic drugs comprising methadone and at least one branched chain amino acid selected from the group consisting of leucine, isoleucine, and valine, wherein the branched chain amino acid is present in an amount of from about 1 to 100% of the solution.

10. The solution of claim 9, wherein the methadone is present in a dosage amount of from about 10 to 80 mg/kg of body weight/day.

11. The solution of claim 9, wherein the branched chain amino acids are leucine, isoleucine, and valine and are present in a ratio by weight of about 0.1–10:0.1–10:0.1–10.

* * * * *